United States Patent
Vermeulen (10) Patent No.: US 11,998,300 B2
(45) Date of Patent: Jun. 4, 2024

(54) OPTICAL METHOD FOR GINGIVITIS DETECTION

(71) Applicant: KONINKLIJKE PHILIPS N.V., Eindhoven (NL)

(72) Inventor: Olaf Thomas Johan Antonie Vermeulen, Oss (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 594 days.

(21) Appl. No.: 17/275,216

(22) PCT Filed: Sep. 4, 2019

(86) PCT No.: PCT/EP2019/073534
§ 371 (c)(1),
(2) Date: Mar. 11, 2021

(87) PCT Pub. No.: WO2020/053042
PCT Pub. Date: Mar. 19, 2020

(65) Prior Publication Data
US 2022/0054015 A1    Feb. 24, 2022

Related U.S. Application Data

(60) Provisional application No. 62/729,446, filed on Sep. 11, 2018.

(51) Int. Cl.
*A61B 5/00* (2006.01)
*G01N 21/31* (2006.01)
*G01N 21/47* (2006.01)

(52) U.S. Cl.
CPC ....... *A61B 5/0088* (2013.01); *G01N 21/3151* (2013.01); *G01N 21/47* (2013.01)

(58) Field of Classification Search
CPC ... A61B 5/0088; A61B 5/4552; A61B 5/7282; A61B 5/7264; A61B 5/1459; A61B 1/24;
(Continued)

(56) References Cited

U.S. PATENT DOCUMENTS 5,040,539 A * 8/1991 Schmitt ................. A61B 5/352
600/340
5,149,503 A * 9/1992 Kohno ............... A61B 5/14557
436/66

(Continued)

FOREIGN PATENT DOCUMENTS

WO   2004084752 A2   10/2004
WO   2015069704 A1   5/2015

OTHER PUBLICATIONS

International Search Report and Written Opinion, International Application No. PCT/EP2019/0735345, dated Nov. 25, 2019.
(Continued)

*Primary Examiner* — Nicholas D Lucchesi (57) ABSTRACT

A tissue inflammation detection system (600) including: a light emitter (602) configured to emit light towards tissue (604); at least one light detector (606) configured to detect diffuse reflective light from the tissue; and a controller (613) including a tissue inflammation detection unit (614) configured to analyze the detected diffuse reflective light in its spectral components. The tissue inflammation detection unit is configured to: determine a tissue contribution from a first wavelength region of a diffuse reflective spectroscopy signal where the diffuse reflective spectroscopy signal is dominated by tissue; extrapolate the tissue contribution to a second wavelength region where the diffuse reflective spectroscopy signal includes at least one detectable hemoglobin absorption feature; subtract the extrapolated tissue contribution from the diffuse reflectance signal; and determine the degree of tissue inflammation.

14 Claims, 4 Drawing Sheets

(58) Field of Classification Search
CPC ..... A61B 1/04; A61B 1/0684; A61B 1/00066; A61B 1/00009
See application file for complete search history.

(56) References Cited

U.S. PATENT DOCUMENTS

| | | | | |
|---|---|---|---|---|
| 5,284,137 | A * | 2/1994 | Kessler | G01N 21/314 128/898 |
| 5,413,100 | A * | 5/1995 | Barthelemy | A61B 5/14551 600/326 |
| 5,570,182 | A | 10/1996 | Nathel et al. | |
| 5,692,503 | A * | 12/1997 | Kuenstner | A61B 5/14551 356/41 |
| 6,122,042 | A * | 9/2000 | Wunderman | A61B 1/0684 356/73 |
| 8,073,212 | B2 * | 12/2011 | Gerlach | A61B 5/0088 382/128 |
| 10,039,489 | B2 | 8/2018 | Guan et al. | |
| 2003/0236647 | A1 * | 12/2003 | Yoon | G01N 21/31 702/183 |
| 2006/0045796 | A1 | 3/2006 | Anderle et al. | |
| 2008/0004511 | A1 * | 1/2008 | Rubinstein | A61K 49/0034 600/309 |
| 2009/0054908 | A1 * | 2/2009 | Zand | A61B 5/7275 600/300 |
| 2010/0280392 | A1 * | 11/2010 | Liu | A61B 5/0088 600/475 |
| 2011/0124987 | A1 | 5/2011 | Papazoglou et al. | |
| 2012/0130208 | A1 * | 5/2012 | Kuhn | A61B 5/14551 600/310 |
| 2012/0184831 | A1 * | 7/2012 | Seetamraju | A61B 5/0075 600/479 |
| 2013/0096403 | A1 * | 4/2013 | Dacso | A61B 5/14551 600/326 |
| 2013/0204102 | A1 * | 8/2013 | Sen | A61B 5/1455 600/322 |
| 2014/0073891 | A1 * | 3/2014 | Stoddart | A61B 5/14551 600/328 |
| 2015/0038350 | A1 * | 2/2015 | Nishinaga | G01N 33/5302 506/10 |
| 2016/0270716 | A1 * | 9/2016 | Guan | A61B 1/000094 |

OTHER PUBLICATIONS

Hanioka, T. et al., "Hemoglobin concentration and oxygen saturation of clinically healthy and inflamed gingiva in human objects", Journal of Periodontal Research, vol. 25, No. 2, Mar. 1, 1990.

Lobene, R. et al., "A modified gingival index for use in clinical trials", Clin. Prev. Dent. 8: 3-6, 1986.

Jones, R. et al., "Near-infrared transillumination at 1310-nm for the imaging of early dental decay", Department of Preventive and Restorative Dental Sciences, University of California, San Francisco, CA 94143, 2003.

\* cited by examiner

OPTICAL METHOD FOR GINGIVITIS DETECTION

This application is the U.S. National Phase application under 35 U.S.C. § 371 of International Application No. PCT/EP2019/073534, filed on 9 Apr. 2019, which claims the benefit of U.S. Provisional Application No. 62/729,446, filed 9 Nov. 2018. These applications are hereby incorporated by reference herein.

FIELD OF THE INVENTION

The present disclosure is directed generally to oral healthcare systems and methods for detecting the presence of tissue inflammation, and gingivitis specifically, using diffuse reflected light.

BACKGROUND

Gingivitis detection using diffuse reflective spectroscopy (DRS) is currently performed with small, angled probes configured around one or more optical fibers which transport light due to the limited space in an oral cavity. Such small probes are useful for measuring at the interproximal areas where gingivitis commonly originates. However, when in contact, such small probes can exert a large pressure on the tissue, pushing away the blood and thereby disrupting the DRS measurement of blood properties. Thus, DRS measurements are preferably taken in non-contact mode. The required non-contact mode leads to detecting unwanted specular reflected light in addition to the desired diffuse reflected component. Since diffuse reflected light (i.e., light propagated through tissue) is highly attenuated, these unwanted specular components can become relatively large.

Furthermore, an important property of the DRS probe is the source-detection separation because it influences the sampling depth of the probe (i.e., from how deep in the tissue the measured light originates). However, the source-detection separation increases the risk of illuminating and/or detecting light from non-gingival tissue, e.g., teeth and or dental implants. For example, because the papilla ends in a small tip-like shape, it is likely that, due to the fiber separation, the desired papilla signal is at least partially contaminated with tooth enamel signals.

Besides the source-detector separation, the sampling depth is limited by the wavelengths used. Short wavelengths (e.g., blue) are highly absorbed by hemoglobin, so they limit the optical path length/depth. Long wavelengths (e.g., NIR) give low scattering coefficients from tissue thereby limiting the amount of light reaching the detector through diffuse scattering (i.e., most is transmitted in the forward direction). Therefore, to measure blood properties from the correct depth, both source-detector distance and wavelengths must be considered. Since gingivitis mostly starts in the gingival sulcus (pockets) thereby disabling direct access to the inflamed site, a certain source-detector separation in combination with a certain wavelength is required. Moreover, these wavelengths must be located at specific hemoglobin absorption features. However, it is desirable to keep the number of wavelengths required as small as possible due to cost and space constraints for oral healthcare systems for consumers.

Accordingly, there is a continued need in the art for inventive oral healthcare systems and methods for detecting moderate tissue inflammation using a DRS method that is insensitive to specular reflections and which uses a limited number of wavelengths.

SUMMARY OF THE INVENTION

The present disclosure is directed to inventive systems and methods for detecting tissue inflammation, and gingivitis specifically, using diffuse reflective spectroscopy (DRS). Various embodiments and implementations herein are directed to methods to accurately detect gingivitis that are robust against specular reflections and use only a minimum number of wavelengths. In addition, the methods which enable accurate gingivitis detection from DRS signals have lower sensitivity to light originating from dental hard tissue and enable a certain degree of freedom in wavelength selection.

Generally, in one aspect, a system for detecting tissue inflammation is provided. The system includes a light emitter configured to emit light towards tissue; at least one light detector configured to detect diffuse reflective light reflected from the tissue; and a controller having a tissue inflammation detection unit configured to analyze the detected diffuse reflective light in its spectral components. The tissue inflammation detection unit is configured to: determine a tissue contribution from a first wavelength region of a diffuse reflective spectroscopy signal where the diffuse reflective spectroscopy signal is dominated by tissue; extrapolate the tissue contribution according to a predetermined wavelength-dependent function to a second wavelength region where the diffuse reflective spectroscopy signal includes at least one detectable hemoglobin absorption feature; subtract the extrapolated tissue contribution from the diffuse reflectance signal; and determine the degree of tissue inflammation. In various embodiments, the system is configured to detect gingivitis.

In one embodiment, the tissue inflammation detection unit is configured to determine the tissue contribution at first and second wavelengths which are greater than 665 nm within the first wavelength region.

In one embodiment, the tissue inflammation detection unit is configured to extrapolate the tissue contributions to third and fourth wavelengths within the second wavelength region, where the second wavelength region is lower than the first wavelength region.

In one embodiment, the system further includes a diffuse reflective spectroscopy probe having a source-detector separation that is greater than 300 μm.

Generally, in another aspect, a method for detecting tissue inflammation is provided. The method includes determining, by a controller, a tissue contribution at first and second wavelengths within a first wavelength region of a diffuse reflective spectroscopy signal where the diffuse reflective spectroscopy signal is dominated by tissue; extrapolating, by the controller, the tissue contributions to third and fourth wavelengths within a second wavelength region different than the first wavelength region, where the diffuse reflective spectroscopy signal includes at least one detectable hemoglobin absorption feature; subtracting, by the controller, the extrapolated tissue contributions from the diffuse reflective spectroscopy signal at the third and fourth wavelengths; and determining, by the controller, the degree of tissue inflammation. In various embodiments, the tissue inflammation is gingivitis.

In one embodiment, the method further includes emitting light towards tissue using a light emitter.

In one embodiment, the method further includes detecting, by at least three wavelength-sensitive detectors, diffuse reflective light at the at least first, second, and third wavelengths before the step of determining the tissue contributions.

In one embodiment, the method further includes measuring the diffuse reflective spectroscopy signal by a diffuse reflective spectroscopy probe having a source-detector separation that is greater than 300 μm.

In one embodiment, the first and second wavelengths are longer than the third and fourth wavelengths.

In one embodiment, the step of extrapolating the tissue contributions involves a predetermined wavelength-dependent function.

In one embodiment, the method further includes emitting light towards tissue using at least three light sources emitting light at the first, second, and third wavelengths and detecting, by a single detector, diffuse reflective light emitted by the at least three light emitters.

As used herein for purposes of the present disclosure, the term "controller" is used generally to describe various apparatus relating to the operation of an apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of systems and methods for improved detection of tissue inflammation, and gingivitis specifically, using diffuse reflected light. More generally, Applicant has recognized and appreciated that it would be beneficial to provide such systems and methods that are insensitive to unwanted specular reflections and that use a limited number of wavelengths. Accordingly, the systems and methods described or otherwise envisioned herein provide an oral healthcare device configured to obtain measurements of gingival tissue. The oral healthcare device includes a light emitter, at least one light detector, and a controller programmed with a specialized algorithm to analyze the received light in its spectral components. The controller is broadly configured to: (i) determine a tissue contribution using wavelengths where blood contribution is minimal, (ii) extrapolate this contribution to another wavelength region where the DRS signal shows a clear hemoglobin absorption feature, (iii) subtract the extracted tissue contribution from the reflected signal to obtain a blood contribution, and (iv) determine one or more hemoglobin parameters using the blood contribution.

The embodiments and implementations disclosed or otherwise envisioned herein can be utilized with any suitable oral healthcare device. Examples of suitable oral healthcare devices include a toothbrush, a flossing device, an oral irrigator, a tongue cleaner, or other personal care device or dental professional oral healthcare device. However, the disclosure is not limited to these oral healthcare devices, and thus the disclosure and embodiments disclosed herein can encompass any oral healthcare device.

Gingivitis, which is an inflammation of the gums, characterized by swollen gums, edema, and redness, is primarily caused by plaque build-up, mostly in the gingival sulcus (pockets). Such gum disease is typically found in areas that are hard to reach, such as interproximal areas between the teeth, and around the back teeth.

Indeed, it is estimated that 50%-70% of the adult population is affected by gingivitis. However, consumers are often unable to detect early signs of gingivitis. Typically, gingivitis progresses until individuals notice their gums bleeding easily when brushing their teeth. Accordingly, gingivitis may only be detected when the disease is already advanced and significantly harder to treat. Although gingivitis is readily reversed by improved oral hygiene, as gingivitis can propagate to irreversible periodontitis it is important to keep good oral health and detect gingivitis as soon as possible.

Gingivitis may be visually diagnosed by detecting reddening and swelling of the gingiva. (see R R. Lobene, et al., "A modified gingival index for use in clinical trials", Clin. Prev. Dent. 8:3-6, (1986) describing a non-contact gingivitis index, based on reddening and inflammation of the gingiva). However, this index has limited sensitivity and is highly dependent on the color rendering index of the light source used. Thus, modern phosphor-converted LEDs can have a low Core Rendering Index (CRI), resulting in poor visual judgments.

The reddening of the gingiva is an acute inflammatory response to bacterial biofilm toxins from plaque in the gingivae sulcus or regions along the gum line. This inflammatory response in the short term causes vasodilation, where smooth muscle cells in the arterioles relax, and widen the blood vessels to increase blood supply to the capillary bed. This gives the reddening of the gingiva, and can give a small temperature increase, which is difficult to measure. In addition, the capillaries become more permeable, which results in increased fluid loss from the capillaries to the interstitial spaces, resulting in the swelling of the gums. If the inflammation is chronic, then additional reddening occurs by increased vascularization of the tissue, where additional capillaries may be formed to cope with the additional blood demands of the tissue.

These factors enable detection of gingivitis based on diffuse reflective spectroscopy (DRS). DRS is an optical method that involves emitting, for example, white light towards a target and analyzing spectral properties of the diffuse (rather than specular) reflected light. Due to the different chromophores in the gingival tissue, the spectral properties of the diffuse reflected light clearly differ from those of the source light. As described in T. Hanioka, et al., "Hemoglobin concentration and oxygen saturation of clinically healthy and inflamed gingiva in human subjects", J. Periodontal Res. 25: 93-98 (1990)), increased total-hemoglobin concentration and decreased blood oxygenation can be determined related to gingivitis detection. This method uses six fixed wavelengths and calculates deoxygenated-, oxygenated-, and total hemoglobin concentrations. The latter two are used to calculate oxygen saturation.

Figure 1A:
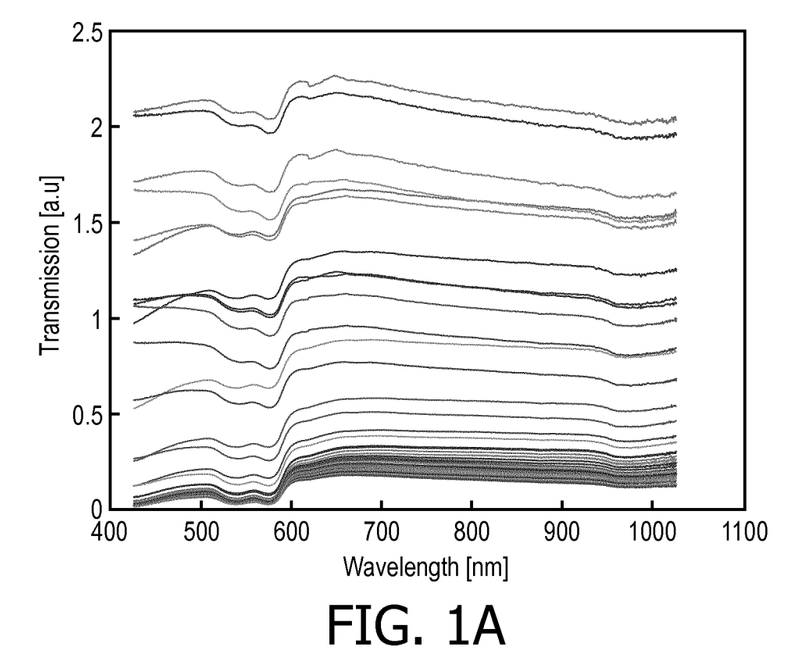
FIG. 1A is a graphical representation of diffuse reflective spectroscopy spectra measured with different probe-to-target angles, in accordance with an embodiment.
Figure 1B:
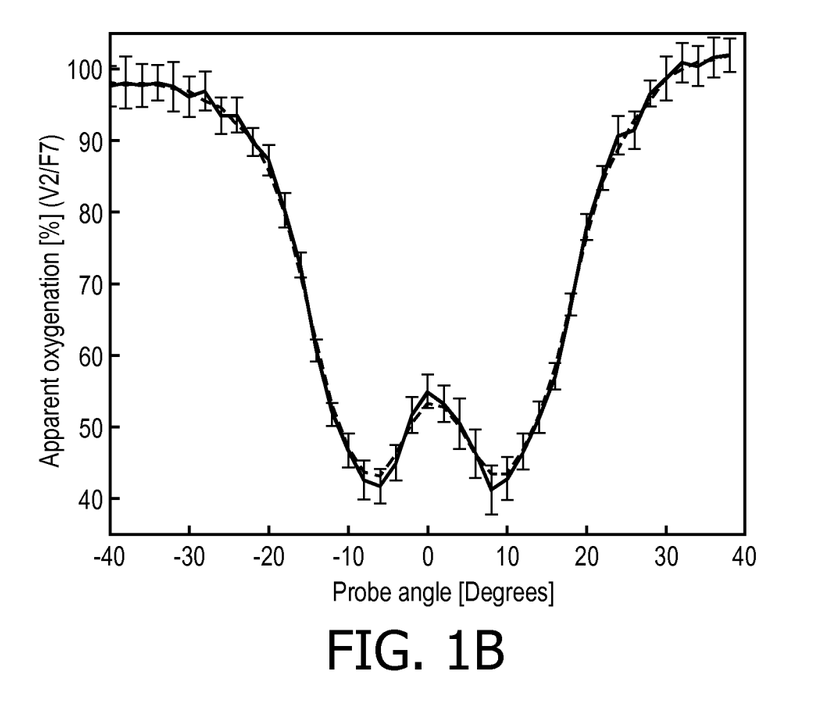
FIG. 1B is a graphical representation of calculated blood oxygenation values, in accordance with an embodiment.

FIGS. 1A and 1B show measured DRS spectra using different probe-to-target angles. In FIG. 1A, the specular reflection is achromatic and results in an offset for each DRS spectrum. In FIG. 1B, blood oxygenation values are calculated according to the example method described in Hanioka. For angles close to the surface normal, the specular reflection becomes approximately ten times larger than the diffuse component. In FIG. 1B, the oxygenation values calculated according to this method produce a large variation. It is clear that specular reflections can lead to large errors.

According to embodiments using wavelength detection, some systems include a spectrometer to analyze the spectral shape of the received light. Other systems include a tunable filter (e.g., a MEMS Fabry-Perot filter) on the received and/or emitted light. Although using a spectrometer or a tunable filter is desirable due to the large number of wavelengths available for processing, currently available systems are too big and/or expensive for consumer products. Alternatively, other systems include color sequential illumination where each color comprises the spectral band required for the analysis. Another option is to split the received light into different paths and apply bandpass filters to achieve the required spectral bands. With respect to these other options, it is desirable to keep the number of wavelengths required as small as possible due to cost and space constraints for oral healthcare systems for consumers.

A particular goal of utilization of certain embodiments of the present disclosure is to enable accurate gingivitis detection from DRS signals that is insensitive to specular reflections, has lower sensitivity to light originating from dental hard tissue, uses a minimum number of wavelengths, and enables a degree of freedom in wavelength selection.

Figure 2:
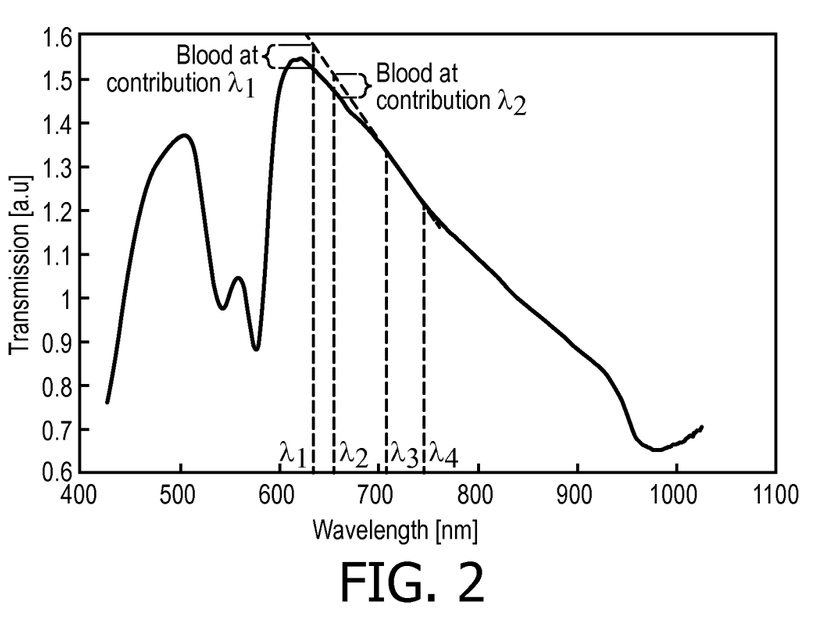
FIG. 2 shows a graphical representation of a diffuse reflective spectroscopy spectrum, in accordance with an embodiment.
Figure 3:
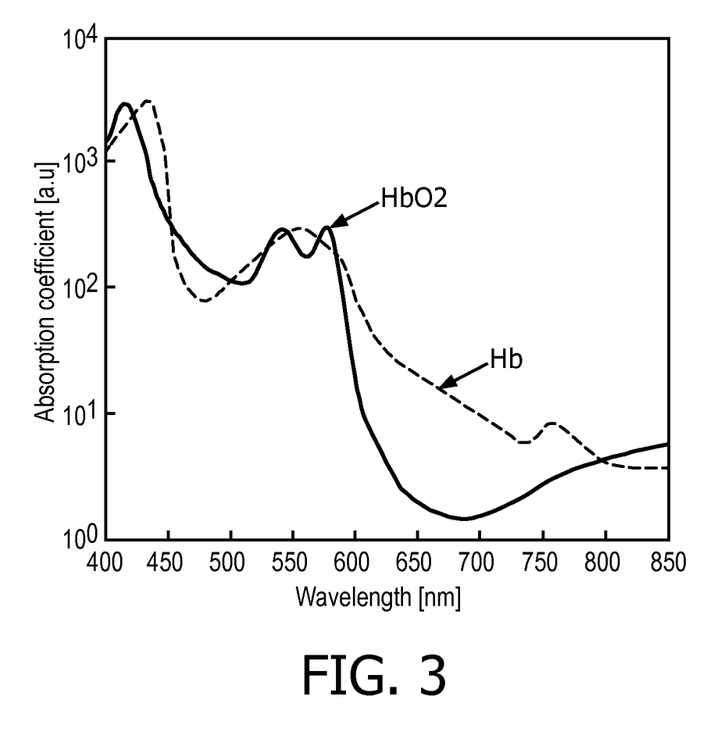
FIG. 3 shows a graphical representation of absorption spectra, in accordance with an embodiment.
Figure 4:
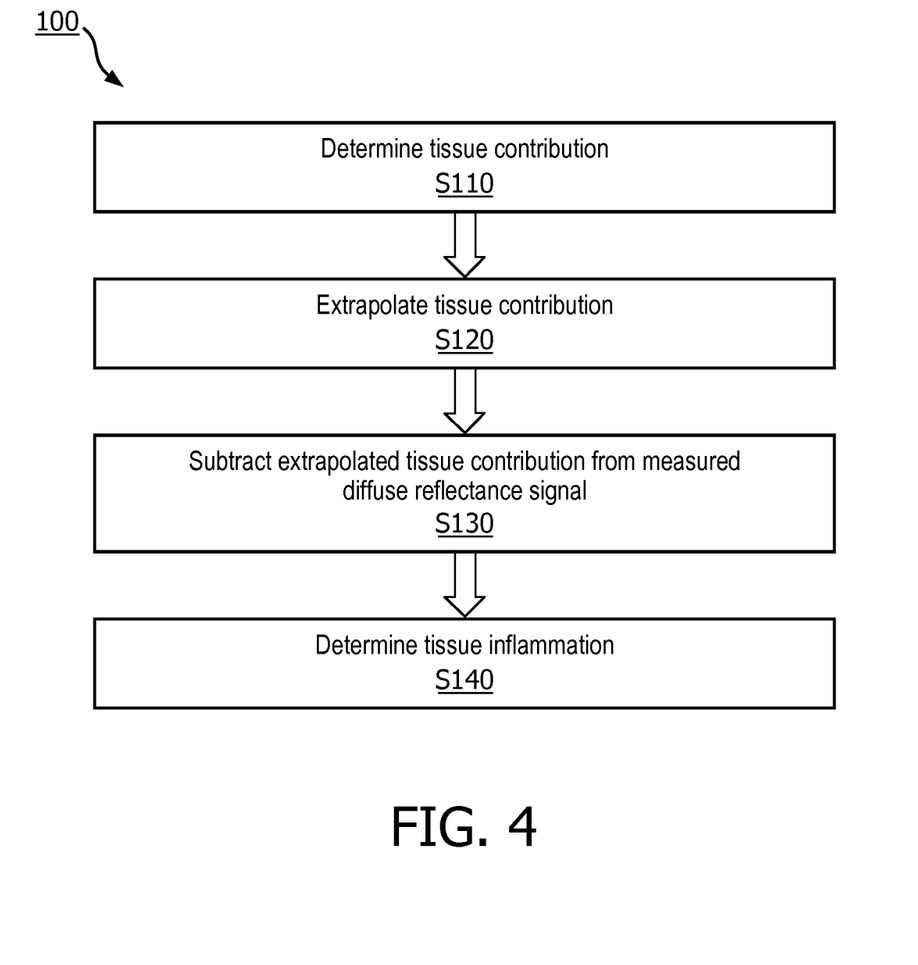
FIG. 4 is a flowchart of a method for determining tissue inflammation for detecting gingivitis, in accordance with an embodiment.

Referring to FIGS. 2, 3, and 4, in one embodiment, is a method for detecting gingivitis using diffuse reflected light. FIG. 2 shows a measured DRS spectrum. FIG. 3 shows absorption spectra of hemoglobin, both oxy-hemoglobin and deoxy-hemoglobin. FIG. 4 shows a flowchart of steps for detecting gingivitis using diffuse reflected light. Since specular reflection is achromatic, it shows a DC offset in the DRS signal. It is clear that, allowing for some error, the contribution of tissue (i.e., scattering and melanin absorption and water below 940 nm) can be modelled using a suitable linear function. For the longer wavelengths, the reflected signal is dominated by tissue (i.e., blood absorption has low significant contribution). Based on the above, it is proposed to determine a tissue contribution using wavelengths where blood contribution is minimal, extrapolate this contribution to another wavelength region where the DRS signal shows a clear hemoglobin absorption feature, subtract the extracted tissue contribution from the reflected signal to obtain a blood contribution, and use the tissue blood contribution to compute hemoglobin parameters.

As can be seen in FIG. 3, the region between 600 nm and 650 nm shows large differences between oxygenated and deoxygenated hemoglobin absorption while still being reasonably relevant absorption levels. From around 650 nm onwards, the absorption in hemoglobin becomes so low that the DRS spectrum is dominated by tissue. Starting from approximately 915 nm onwards water becomes dominant. Referring to FIG. 2, in this example, four wavelengths are chosen from the red/near-infrared (NIR) region; two within a first wavelength region, and two within a second wavelength region. By taking two wavelength readings in each region, comparison calculations can be performed easily; however, it can be appreciated that a calculations can be compared using a total of at least three wavelengths, or even more than four wavelengths. The longer two wavelengths (709 nm and 745 nm in the example shown in FIG. 2) are used to extrapolate the assumed tissue contribution to the red region. Then, at the shorter two wavelengths (632 nm and 655 nm), a blood contribution can be calculated by subtracting the DRS signal from the extrapolated tissue contribution. Next, using the known absorption coefficients for hemoglobin and the calculated blood contributions, the desired de-oxy and oxy-hemoglobin concentrations [Hb] and [HbO2] can be calculated.

Figure 5:
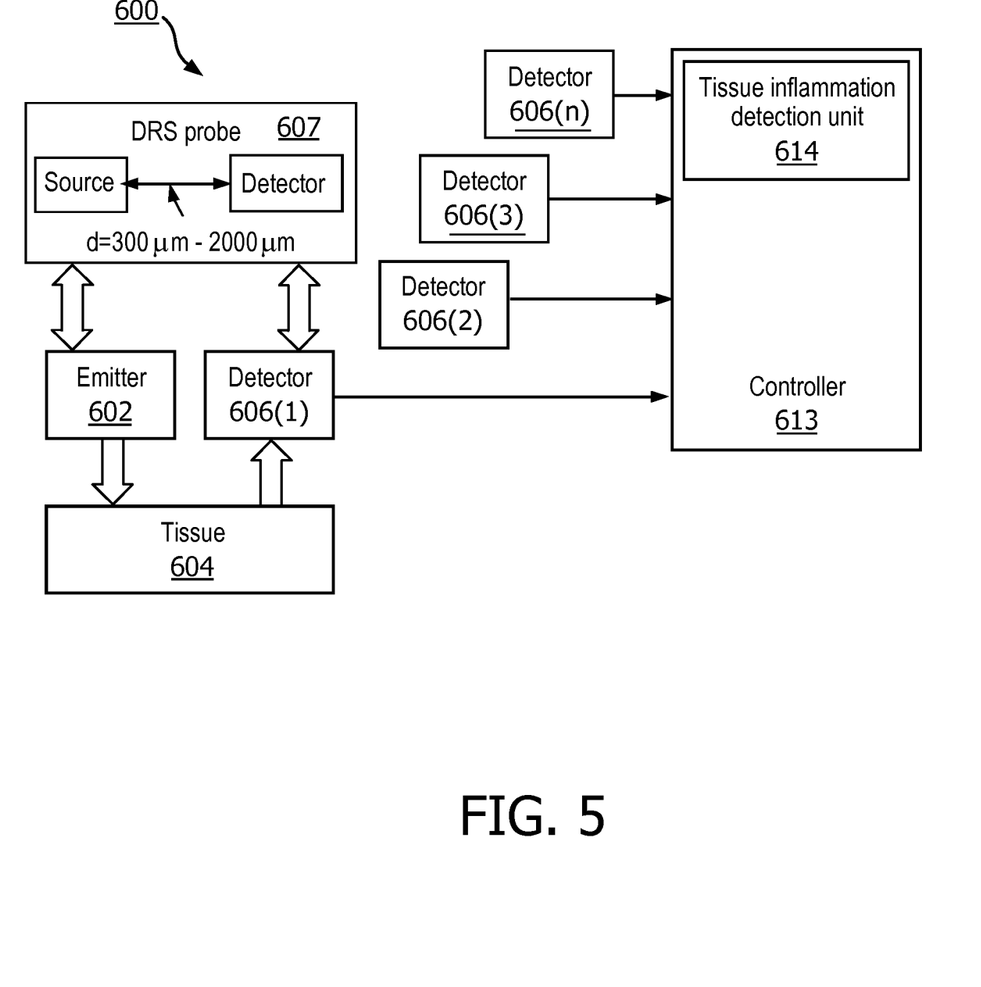
FIG. 5 is a schematic representation of a system for detecting gingivitis, in accordance with an embodiment.

Referring to FIG. 4, in one embodiment, is a flowchart of steps for a method 100 for detecting gingivitis using diffuse reflected light. According to an embodiment, a system 600, such as shown in FIG. 5, which has one or more light emitters and light detectors is provided to detect diffuse reflected light from gingiva and the detected light is communicated or otherwise transmitted to a controller for processing or analysis. At step S110 of the method, a controller or analyzer 613 (as shown in FIG. 5) determines a tissue contribution from a wavelength region where hemoglobin has relatively low absorption. A tissue slope can be calculated as follows:

$$\alpha(\text{tissue slope}) = (Rp^{\lambda_4} - Rp^{\lambda_3})/(\lambda_4 - \lambda_3) \quad (1)$$

where $Rp_\lambda$ represents a measured diffuse reflectance at wavelength $\lambda$ and $\lambda_1 \ldots \lambda_n$ represents sample wavelength with $n \geq 4$. Using the example shown in FIG. 2, the longer two wavelengths (709 nm and 745 nm) can be used.

At step S120 of the method, the controller or analyzer extrapolates the tissue contribution according to a predetermined wavelength-dependent function to another region in the spectrum having one or more detectable hemoglobin absorption features. Using the example shown in FIG. 2, the tissue contribution is extrapolated to two shorter wavelengths (632 nm and 655 nm). The extrapolation can be calculated as follows:

$$T_{\lambda_b} = Rp_{\lambda_t} + (\lambda_b - \lambda_t) \cdot \alpha \quad (2)$$

where $T_{\lambda_b}$ represents extrapolated tissue contributions at $\lambda_b$.

At step S130 of the method, the controller or analyzer subtracts the extrapolated tissue contribution at the shorter two wavelengths from the measured diffuse reflectance signal to obtain a tissue blood contribution at the two shorter wavelengths according to the following calculation:

$$B_{\lambda_b} = T_{\lambda_b} - Rp_{\lambda_b} \quad (3)$$

where $B_{\lambda_b}$ represents tissue blood contribution calculated at wavelength $\lambda_b$. In the example depicted in FIG. 2, the two shorter wavelengths are 632 nm and 655 nm. Since both terms in the subtraction in equation (3) contain an equal specular reflection contribution, the calculated blood contribution is free of a specular reflection contribution.

At step S140 of the method, the controller or analyzer determines hemoglobin parameters to ascertain tissue inflammation. For example, oxygenated and deoxygenated concentrations can be determined using known absorption coefficients for hemoglobin and the calculated tissue blood contributions at 632 nm and 655 nm. The following calculations can be used to determine oxygenated and deoxygenated concentrations, respectively:

$$[HbO_2] = \frac{B_{\lambda_1} \cdot \mu a_{\lambda_2}^{Hb} - B_{\lambda_2} \cdot \mu a_{\lambda_1}^{Hb}}{\mu a_{\lambda_1}^{HbO2} \cdot \mu a_{\lambda_2}^{Hb} - \mu a_{\lambda_2}^{HbO2} \cdot \mu a_{\lambda_1}^{Hb}} \quad (4)$$

$$[Hb] = \frac{B_{\lambda_1} \cdot \mu a_{\lambda_2}^{HbO2} - B_{\lambda_2} \cdot \mu a_{\lambda_1}^{HbO2}}{\mu a_{\lambda_2}^{HbO2} \cdot \mu a_{\lambda_1}^{Hb} - \mu a_{\lambda_1}^{HbO2} \cdot \mu a_{\lambda_2}^{Hb}} \quad (5)$$

To obtain a total hemoglobin concentration, the determined oxygenated and deoxygenated concentrations can be added together as follows:

$$[Hbt] = [Hb] + [HbO2] \quad (6)$$

The oxygen saturation can be determined according to the following calculation:

$$SO2 = 100\% * [HbO2]/[Hbt] \quad (7)$$

According to an embodiment, as an alternative to determining the oxygenated and deoxygenated concentrations from the remainder blood contributions at 632 nm and 655 nm as described in (4) and (5) above, an isosbestic wavelength $\lambda_1$, for example, 584 nm and 800 nm (which can limit the wavelength choice) can also be used to determine the total hemoglobin concentration and the oxygenated and deoxygenated concentrations as follows:

$$[Hbt] = \frac{B_{\lambda_1}}{\mu a_{\lambda_1}^{Hb}}$$

$$[HbO_2] = \frac{B_{\lambda_2} - [Hbt] \cdot \mu a_{\lambda_2}^{Hb}}{\mu a_{\lambda_2}^{HbO2} - \mu a_{\lambda_2}^{Hb}}$$

$$[Hb] = \frac{B_{\lambda_2} - [Hbt] \cdot \mu a_{\lambda_2}^{HbO2}}{\mu a_{\lambda_2}^{Hb} - \mu a_{\lambda_2}^{HbO2}}$$

All computations (except the intermediate interpolated tissue value) are independent of offset (specular reflection). In all calculations, it is assumed that the optical path length is equal everywhere. Additionally, the calculated values are not real, but rather they represent apparent values. Thus, advantageously, the inventive systems and methods described herein enable accurate gingivitis detection from DRS signals which is insensitive to specular reflections. Accordingly, the inventive systems and methods as described herein are less sensitive to light originating from non-gingival tissue or dental hard tissue.

The number of wavelengths selected can be equal to or greater than four (≥4) to increase accuracy, e.g., by noise reduction and/or using higher order polynomial for tissue extrapolation. Advantageously, while the inventive systems and methods described herein enable accurate gingivitis detection from DRS signals using four wavelengths as an example, which is more cost effective than conventional systems that use more wavelengths, systems using three wavelengths are also feasible using the inventive systems and methods disclosed herein. In addition, the inventive systems and methods described herein enable a certain degree of freedom with respect to the selection of the wavelengths used.

As described herein, in order to detect gingivitis it is desirable to achieve a sufficiently deep sampling depth with a source-detector separation >300 μm using the lower hemoglobin absorbing red/NIR wavelengths, i.e., not using the highly absorbing blue and green wavelength region. Referring to FIG. 5, in one embodiment, is an example system 600 for detecting tissue inflammation and gingivitis. System 600 includes a light emitter 602 and multiple discrete wavelength-sensitive detectors $606_{1-n}$. The examples described herein refer to a system and method using four discrete wavelengths, although a system using more than four wavelength-sensitive detectors can be used, and a system using three wavelengths can also be used. In the examples described herein, four discrete wavelength-sensitive detectors are described—two in a first wavelength region, and two in a second wavelength region. Emitter 602 includes a single broadband source configured to emit light towards tissue 604. According to an embodiment with four wavelengths, detectors $606_{1-n}$ are configured to detect diffuse reflected light from tissue 604 at wavelengths 655 nm, 632 nm, 709 nm, and 745 nm, respectively. Detector $606_1$ can be configured to detect λ1 at 709 nm, detector 6062 can be configured to detect λ2 at 745 nm, detector 6063 can be configured to detect λ3 at 632 nm, and detector 6064 can be configured to detect λ4 at 655 nm. It can be appreciated that any two different wavelengths within the first and second wavelength regions can be used. System 600 further includes a controller 613 having a tissue inflammation detection unit 614 and algorithm such as the one described above.

According to an embodiment, system 600 includes a DRS probe 607 having a source-detector separation that is greater than 300 μm. The source of the probe can be coupled with emitter 602 and the detector of the probe can be configured to deliver the detected light to detectors $606_{1-n}$ via a splitter, for example. Many DRS probe configurations are possible, but the most common consist of one source fiber next to one detection fiber. Other configurations are, e.g., one central source fiber surrounded by six detection fibers or just one single fiber functioning as source and detector simultaneously.

According to an embodiment, system 600 can include three wavelengths for the tissue extrapolation to reduce extrapolation errors, or four, five or more wavelengths. Alternatively, system 600 can include a second degree polynomial for the tissue extrapolation to reduce extrapolation errors.

According to an embodiment, instead of the multiple discrete detectors, system 600 can include a single detector in the form of a tunable bandpass filter (with photodetector), a spectrometer, or any suitable alternative.

According to an embodiment, instead of a single broadband source, system 600 can include four or more separate sources or emitters with the required spectral properties and a single detector at the receiver end.

Advantageously, the inventive systems and methods described herein enable accurate gingivitis detection using a DRS method that is insensitive to specular reflections and uses a limited number of wavelengths.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A system for detecting tissue inflammation, comprising:
    a light emitter configured to emit light towards tissue;
    at least one light detector configured to detect diffuse reflective light reflected from said tissue; and
    a controller comprising a tissue inflammation detection unit configured to analyze the detected diffuse reflective light in its spectral components, said tissue inflammation detection unit configured to:
    determine a tissue contribution from a first wavelength region of a diffuse reflective spectroscopy signal where the diffuse reflective spectroscopy signal is dominated by tissue;
    extrapolate the tissue contribution according to a predetermined wavelength-dependent function to a second wavelength region where the diffuse reflective spectroscopy signal comprises at least one detectable hemoglobin absorption feature;
    subtract the extrapolated tissue contribution from the diffuse reflective spectroscopy signal; and
    determine the degree of tissue inflammation.

2. The tissue inflammation detection system of claim 1, wherein said system is configured to detect gingivitis.

3. The tissue inflammation detection system of claim 1, wherein said tissue inflammation detection unit is configured to determine the tissue contribution at first and second wavelengths which are greater than 665 nm within the first wavelength region.

4. The tissue inflammation detection system of claim 3, wherein said tissue inflammation detection unit is configured to extrapolate the tissue contributions to third and fourth wavelengths within the second wavelength region, where the wavelengths in said second wavelength region are shorter than the wavelengths in said first wavelength region.

5. The tissue inflammation detection system of claim 4, wherein said second wavelength region is 400 nm to 600 nm.

6. The tissue inflammation detection system of claim 1, further comprising a diffuse reflective spectroscopy probe having a source-detector separation that is greater than 300 pm.

7. The tissue inflammation detection system of claim 1, wherein the at least one light detector is at least four wavelength-sensitive detectors, configured to detect diffuse reflective light at said at least first, second, and third wavelengths reflected from said tissue.

8. A method for detecting tissue inflammation, comprising:
- determining, by a controller, a tissue contribution at least a first and second wavelengths within a first wavelength region of a diffuse reflective spectroscopy signal where the diffuse reflective spectroscopy signal is dominated by tissue;
- extrapolating, by the controller, the tissue contributions to at least a third and fourth wavelengths within a second wavelength region where the diffuse reflective spectroscopy signal comprises at least one detectable hemoglobin absorption feature;
- subtracting, by the controller, the extrapolated tissue contributions from the diffuse reflective spectroscopy signal at the at least third and fourth wavelengths to provide blood contributions at the at least third and fourth wavelengths; and
- determining, by the controller, the degree of tissue inflammation based on first and second blood contributions.

9. The method of claim 8, wherein the tissue inflammation is gingivitis.

10. The method of claim 8, further comprising the step of detecting, by four wavelength-sensitive detectors, diffuse reflective light at said at least first, second, third, and fourth wavelengths prior to the step of determining the tissue contributions.

11. The method of claim 8, wherein said first and second wavelengths are longer than said third and fourth wavelengths.

12. The method of claim 8, wherein the step of extrapolating the tissue contributions involves a predetermined wavelength-dependent function.

13. The method of claim 8, further comprising the step of emitting light towards tissue using at least four light sources emitting light at said first, second, third, and fourth wavelengths.

14. The method of claim 13, further comprising the step of detecting, by at least one detector, diffuse reflective light emitted by said at least four light sources.

* * * * *